(12) United States Patent
Tromborg

(10) Patent No.: US 9,636,468 B2
(45) Date of Patent: May 2, 2017

(54) VENIPUNCTURE ASSIST DEVICE

(71) Applicant: Craig Tromborg, Glencoe, MN (US)

(72) Inventor: Craig Tromborg, Glencoe, MN (US)

(*) Notice: Subject to any disclaimer, the term of this patent is extended or adjusted under 35 U.S.C. 154(b) by 0 days.

(21) Appl. No.: 14/889,598

(22) PCT Filed: Apr. 29, 2015

(86) PCT No.: PCT/US2015/028314
§ 371 (c)(1),
(2) Date: Nov. 6, 2015

(87) PCT Pub. No.: WO2015/168300
PCT Pub. Date: Nov. 5, 2015

(65) Prior Publication Data
US 2016/0136362 A1    May 19, 2016

Related U.S. Application Data

(60) Provisional application No. 61/985,845, filed on Apr. 29, 2014.

(51) Int. Cl.
*A61M 5/42* (2006.01)
*A61M 5/32* (2006.01)
*A61B 5/153* (2006.01)

(52) U.S. Cl.
CPC .............. *A61M 5/425* (2013.01); *A61B 5/153* (2013.01); *A61M 5/3287* (2013.01); *A61M 5/42* (2013.01)

(58) Field of Classification Search
CPC ........ A61M 5/427; A61M 5/425; A61M 5/42; A61M 39/00; A61B 5/153; A61M 5/3287; A61B 5/489
See application file for complete search history.

(56) References Cited

U.S. PATENT DOCUMENTS

| | | | |
|---|---|---|---|
| 1,934,046 A | 11/1933 | Demarchi | |
| 2,234,961 A | 3/1941 | Canada | |
| 2,282,853 A | 5/1942 | Clark | |
| 2,945,496 A * | 7/1960 | Fosdal | A61M 5/425 604/115 |
| 4,299,219 A | 11/1981 | Norris, Jr. | |
| 4,664,651 A | 5/1987 | Weinshenker et al. | |

(Continued)

OTHER PUBLICATIONS

United States International Searching Authority; International Search Report for PCT/US2015/28314; issued Sep. 29, 2015; US Patent and Trademark Office; Alexandria, VA; US.

(Continued)

*Primary Examiner* — Bhisma Mehta
*Assistant Examiner* — Hamza Darb
(74) *Attorney, Agent, or Firm* — Underwood & Associates, LLC

(57) ABSTRACT

A venipuncture assist device includes a main body having a first surface configured to confront a target venipuncture site. The device further includes a vein capture channel disposed within the first surface configured to urge a portion of a patient's tissue and subcutaneous vein therein when the vein capture channel is evacuated by vacuum, wherein the urging creates a bend in the vein for piercing by a venipuncture needle. The device further includes one or more needle channels extending from a front main body surface configured to receive and guide the needle into the bend in the vein.

13 Claims, 4 Drawing Sheets

(56) References Cited

U.S. PATENT DOCUMENTS

| | | | |
|---|---|---|---|
| 6,066,116 A | 5/2000 | Fox | |
| 6,254,580 B1 | 7/2001 | Svedman | |
| 6,524,297 B1 | 2/2003 | Newman | |
| 6,579,265 B1 * | 6/2003 | Kihara | A61M 1/16 604/174 |
| 6,652,487 B1 | 11/2003 | Cook | |
| 7,303,576 B2 | 12/2007 | Peters | |
| 7,507,209 B2 * | 3/2009 | Nezhat | A61B 17/3403 600/560 |
| 7,655,023 B2 | 2/2010 | Madison | |
| 7,776,028 B2 * | 8/2010 | Miller | A61M 1/0088 604/313 |
| 7,824,371 B2 | 11/2010 | Perez | |
| 7,842,008 B2 | 11/2010 | Clarke et al. | |
| 8,007,467 B2 | 8/2011 | Rutkowski | |
| 8,197,504 B2 | 6/2012 | Stokes et al. | |
| 8,323,249 B2 | 12/2012 | White et al. | |
| 2008/0243076 A1 | 10/2008 | Goldan et al. | |
| 2009/0198181 A1 | 8/2009 | Bakhtyari-Nejad-Esfahani | |
| 2011/0301500 A1 | 12/2011 | Maguire et al. | |
| 2012/0041377 A1 | 2/2012 | Haak | |
| 2013/0150714 A1 * | 6/2013 | Howlett | A61B 8/4483 600/439 |

OTHER PUBLICATIONS

United States International Searching Authority; Written Opinion of the International Searching Authority for PCT/US2015/28314; US Patent and Trademark Office; Alexandria, VA; US, Sep. 29, 2015.

\* cited by examiner

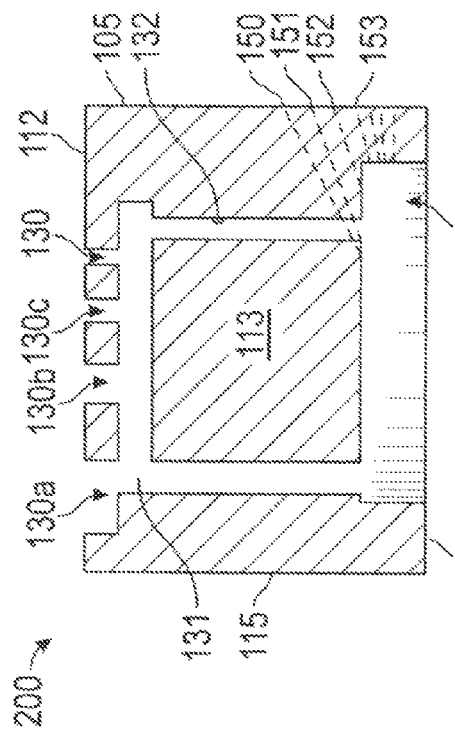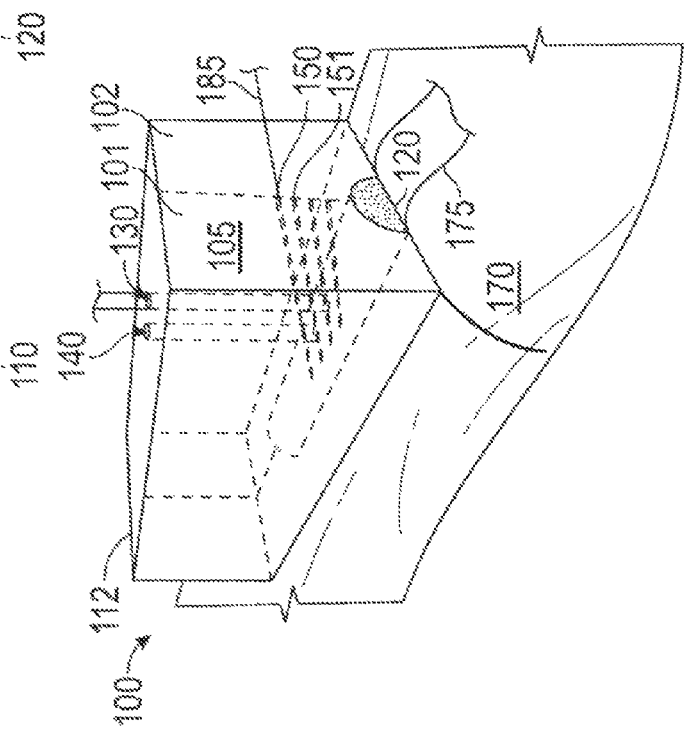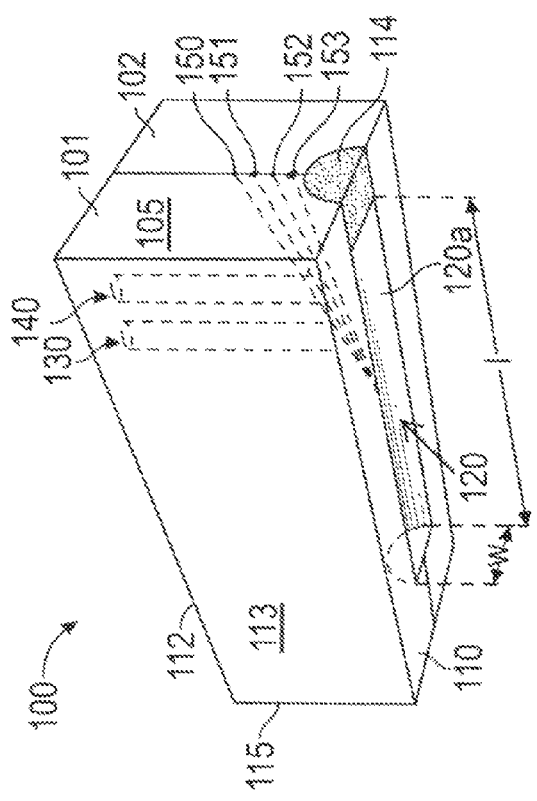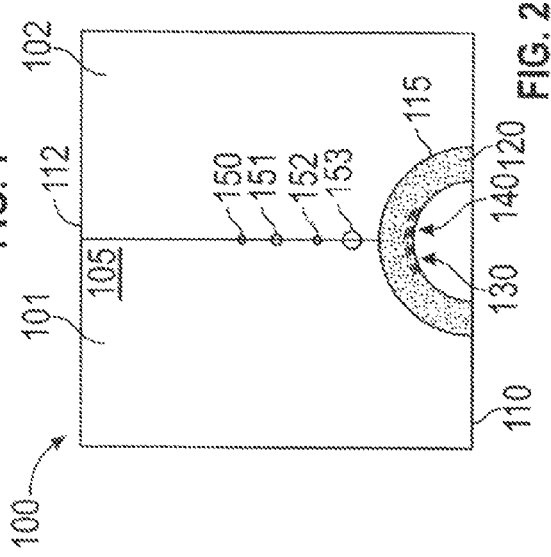

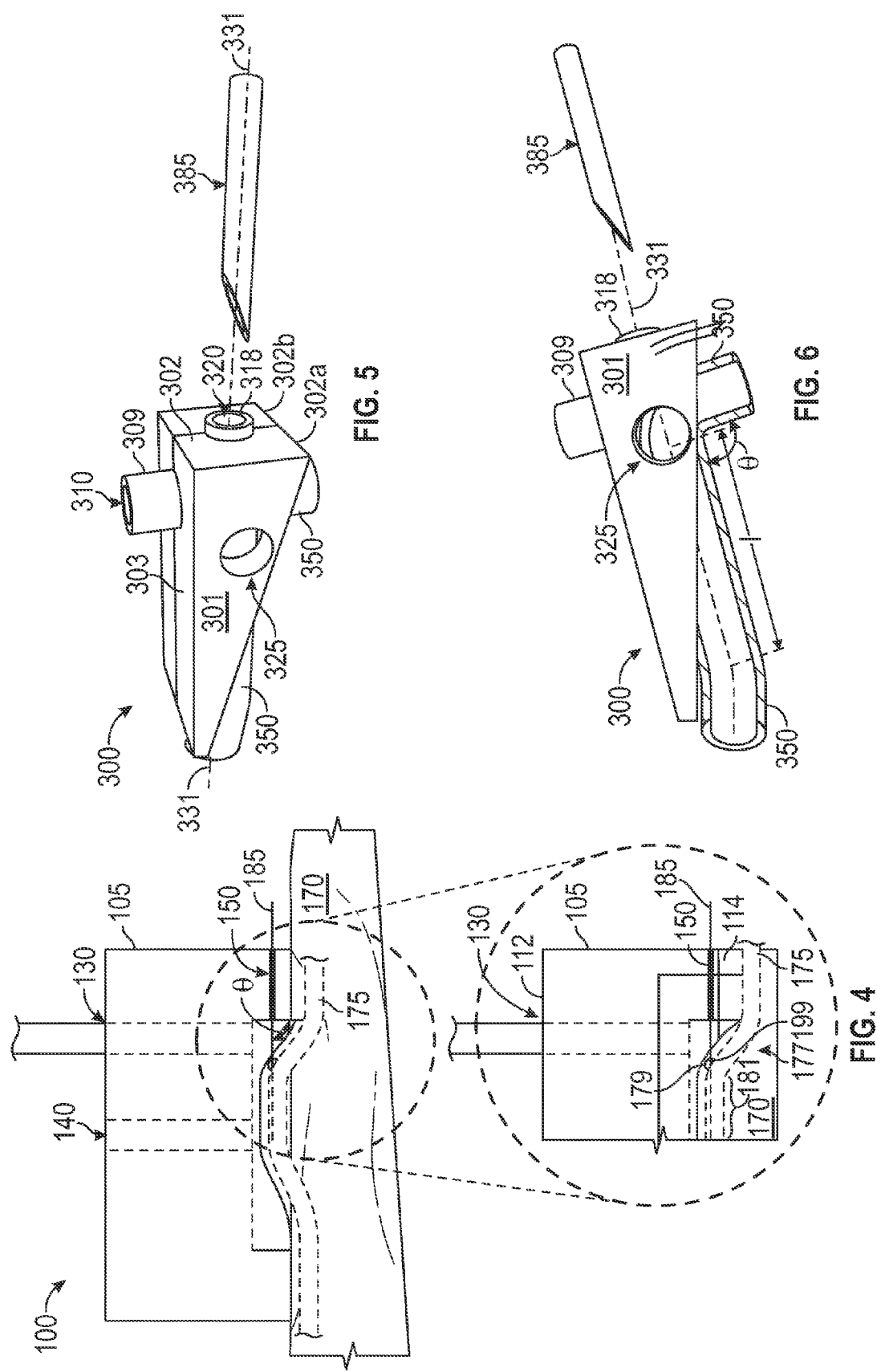

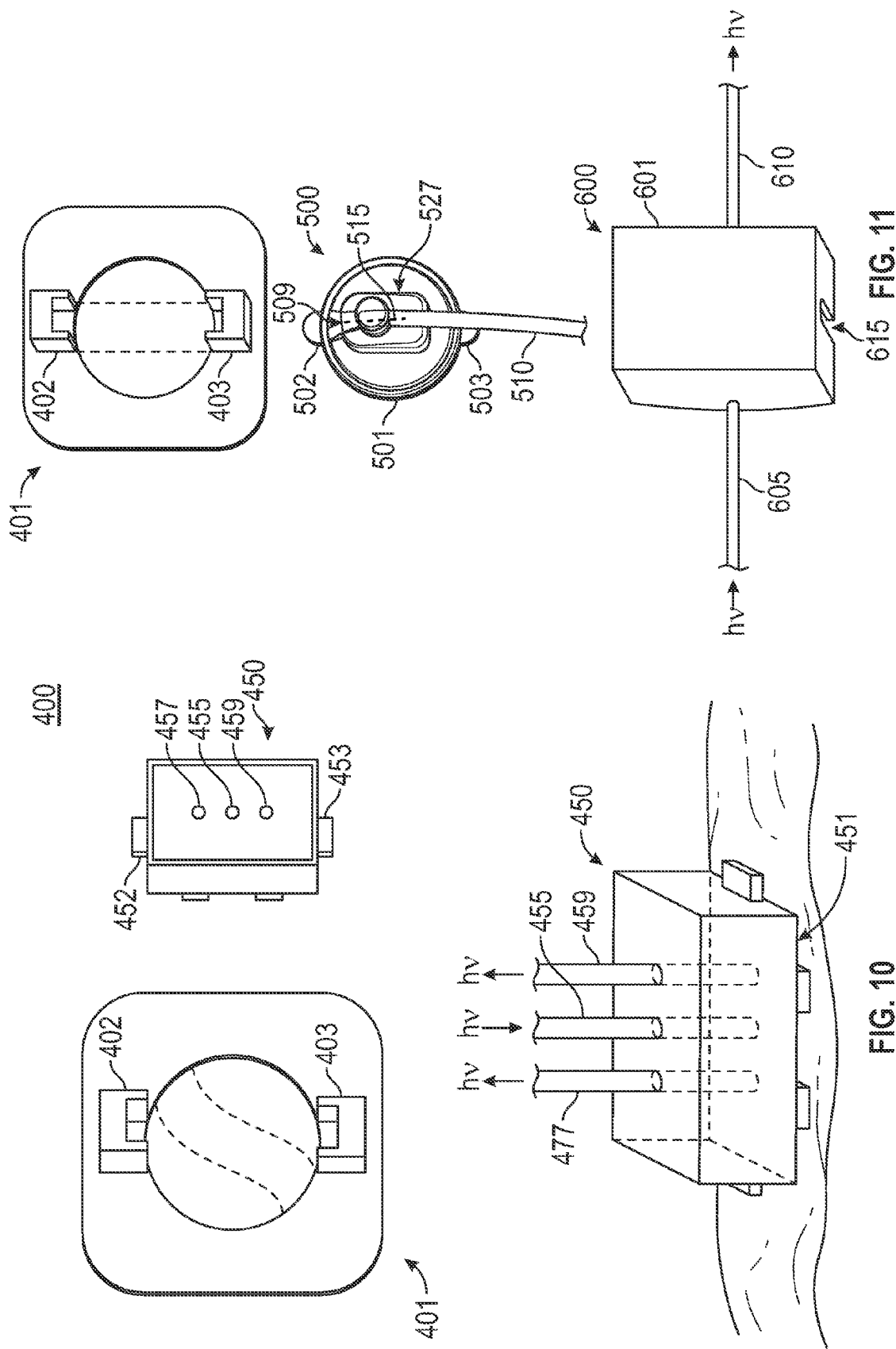

VENIPUNCTURE ASSIST DEVICE

CROSS REFERENCE TO RELATED APPLICATIONS

This application claims priority to and the benefit under 35 USC §119(e) of U.S. Provisional Patent Application No. 61/985,845, filed on Apr. 29, 2014, the contents of which are incorporated by reference in their entirety as if fully set forth herein.

TECHNICAL FIELD

This disclosure relates to systems and methods for performing venipuncture procedures. In particular, this disclosure relates to systems and methods for reliably performing a venipuncture procedure on a subject using a venipuncture assist device.

BACKGROUND

In general, venipuncture is the puncture of a vein, typically for the purpose of withdrawing a blood sample or for injecting one or more substances into the blood stream of a patient. Various morphological aspects of vasculature can vary between subjects. Vein structure, size, rigidity and other anatomical features can differ greatly between human subjects, for example.

Certain patient populations, e.g., elderly and pediatric patients in particular, can have small or fragile vasculature that can make venipuncture particularly difficult for a healthcare provider. In the former population, some elderly patients can have thin, paper-like skin that allows a subcutaneous vein to move about subcutaneously with relative ease. In addition, elderly subjects can have veins that tear or puncture easily, which can increase the skill level required to successfully start intravenous therapy or perform a blood draw. Some pediatric patients, on the other hand, may have very small veins which can require the use of correspondingly small needles and combination needle/catheter systems to successfully perform venipuncture, which again increases venipuncture complexity for health care providers.

Regardless of a patient's particular anatomy, it can be unpleasant when a healthcare practitioner misses a vein or repeats a venipuncture attempt due to the pain it can cause. More importantly, in some cases, time can be a critical component during a medical emergency when rapid injection of intravenous drugs can have a significant effect on patient survivability. A wide range of healthcare provider types, e.g., doctors, nurses, phlebotomists, paramedics, emergency medical technicians (EMT's), and firefighters may be called upon to perform a venipuncture procedure when time is of the essence. Additionally, military personnel may be called upon to start intravenous therapy in the field under difficult and stressful circumstances.

Thus, it can be beneficial to both patient and practitioner that venipuncture be performed quickly, accurately, and reliably, preferably on the first attempt. Such practice can minimize the likelihood of pain from repeated attempts and allow rapid infusion of fluids and pharmacological agents that can have a positive effect on patient treatment and survivability.

SUMMARY

In one exemplary aspect, a venipuncture assist device ('device') is disclosed. In one embodiment, the venipuncture assist device includes a main body having a bottom surface configured to confront a target venipuncture site, e.g., a portion of skin having a subjacent, subcutaneous vein. The device further includes a vein capture channel disposed within the bottom surface configured to receive the target venipuncture site therein when the vein capture channel is evacuated by vacuum. The urging of the skin tissue and subcutaneous physiology into the vein capture channel can create a bend in a subcutaneous vein that forms an optimized needle-piercing configuration, and a substantially straight, elongate insertion axis for the needle, catheter, or both that can reduce the likelihood of extravasation. The device further includes one or more needle channels extending from a second main body surface that are configured to receive and guide the needle into the bend in the vein at an optimized incidence angle for venipuncture.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which:

FIGS. 1, 2, 3 and 4 illustrate a venipuncture assist device, according to one embodiment;

FIG. 1A illustrates a venipuncture device according to one alternative embodiment;

FIGS. 5-9 illustrate a venipuncture device according to one embodiment; and

FIGS. 10-11 illustrate components of a venipuncture assist system according to one embodiment.

DETAILED DESCRIPTION OF ILLUSTRATIVE EMBODIMENTS

Figure 7:
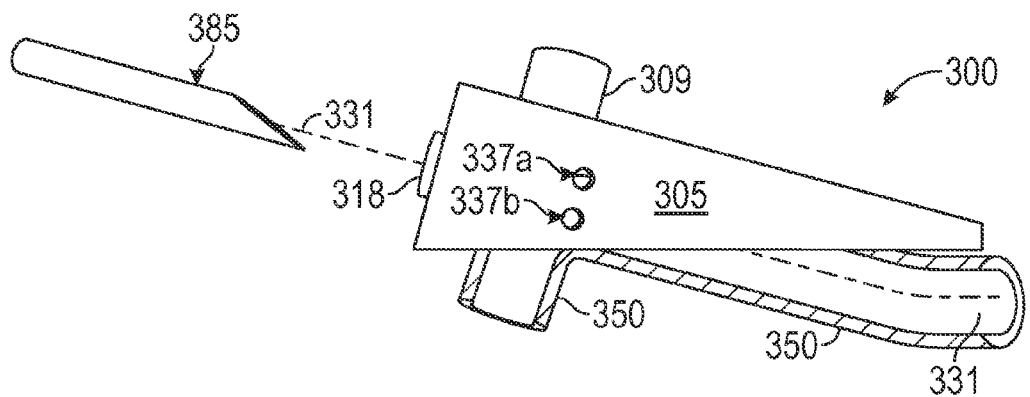

In one exemplary aspect, various embodiments of a venipuncture assist device are disclosed. In the description that follows, it should be understood that various modifications or adaptations can be made to address specific requirements, to perform specific functions or to address desired characteristics in a venipuncture assist device. Thus, this disclosure and corresponding figures are illustrative and non-limiting with respect to the claims.

In one embodiment, a venipuncture device as described herein can include a main body configured, on at least one side, to be confronted with a portion of a patient's skin near a target venipuncture area. The main body can have one or more channels extending from a first main body side to a second, different, main body side, typically, but not necessarily orthogonally arranged, that are each configured to guide a venipuncture needle or a combination needle/catheter system into a subject's vasculature at an optimized approach angle. In this and other embodiments, an optimized approach angle can be an angle that allows, e.g., a venipuncture needle, such as a hypodermic needle, to be inserted at an optimized angle relative to an induced vein configuration that reduces the likelihood of missing the vein altogether or advancing the needle opening past the vein during a venipuncture procedure. In this and other embodiments, an induced vein configuration can be an adjustment of a naturally-occurring vein orientation that is caused by drawing a portion of the patient's physiology, e.g., a portion of the patient's skin, into a recessed portion of the main body in confrontation with the target venipuncture area. In this and other embodiments, such an induced vein configuration can be engendered by urging the patient's skin into the recessed area of the main body using a pressure differential between atmospheric pressure and that inside the main body. Such a pressure differential can be created, e.g., by applying vacuum to the recessed portion of the main body as described in greater detail herein. In this and other embodiments, the one or more channels can be configured with a stop member such that a venipuncture needle can be advanced a desired distance into the patient's vasculature before abutting the stop member. Such a configuration can provide an easy reference that a practitioner may use to prevent the venipuncture needle from being inserted too far into the vasculature, potentially causing extravasation. In this and other embodiments, the main body of a venipuncture assist device can include one or more mechanisms or adaptations configured to substantially immobilize a target portion of a vein, e.g., the basilic or cephalic vein, for a venipuncture procedure.

Referring now to the figures, FIGS. 1 and 2 show perspective and front views, respectively, of a venipuncture assist device (hereinafter "device") 100 according to one embodiment. In this embodiment, the device 100 has a generally cubic-rectangular shape; however, the device may be formed in other shapes and sizes to address desired aspects of style, functionality or other considerations. For example, a bottom face 110, described below, can include a substantially concave curvature configured to substantially match a curvature of the forearm, wrist, or other patient physiology.

In this and other embodiments, the device 100 can be formed of any material suitable for the intended purpose of performing venipuncture as generally described herein. Exemplary, non-limiting materials from which the device 100 can be made include various types of plastics, silicone, including derivatives thereof, glasses, polymers and polymer blends, e.g., poly-methyl methacrylate, and others. In general, it can be advantageous that the device be made from a transparent material so that a practitioner can visualize a target venipuncture site through the device and for other reasons, such as to allow light to propagate therethrough, as discussed herein.

In this embodiment, the device 100 includes, inter alia, a front face 105, a bottom face 110, a top face 112, a left face 113, and a rear face 115 as illustrated. In this embodiment, a recessed vein capture channel 120 is defined by an elongate, substantially concave interior wall 120a having a substantially semi-cylindrical shape between the front face 105 and the rear face 115 as illustrated. The vein capture channel 120 can be configured in shape and size as necessary to provide optimal vein-capturing performance, which may be influenced by factors such as the species of the patient (e.g., human vs. non-human), patient age, the condition of the patient's veins, etc., as will be described in greater detail below. In some embodiments, the vein capture channel 120 can include one or more tapered end portions which can be beneficial in providing a seal between the bottom face 110 and the epidermis.

In this embodiment, the vein capture channel 120 is "close-ended" on opposing terminal end portions, in that proximal and distal ends of the elongate channel terminates at a wall portion extending generally inwardly from the rear face 115 and the front face 105 respectively. In some embodiments, however, one or both ends of the vein capture channel 120 can extend through either the rear (115) or front (105) faces, respectively. Referring specifically to FIG. 1, portion 114 of the device 100 is shown as a shaded portion to illustrate an exemplary section that would be absent in an embodiment where the vein capture channel 120 extended through the front face 105. Such vein capture channel configurations may be beneficial, or provide certain advantages in performing venipuncture on certain subjects.

In this embodiment, the device 100 includes a vacuum port 130 that extends from the top face 112 into the vein capture channel 120 and is configured to provide a pressure differential between the channel 120 and the atmosphere surrounding the device 100 by applied vacuum as described in greater detail below. Other embodiments can include a plurality of vacuum ports disposed about the device 100, also in atmospheric communication with the vein capture channel 120 to achieve optimal vacuum performance or for other advantageous purposes. For example, a vacuum port can be disposed on any face of the device 100 so that a practitioner can control vacuum pressure to the vein capture channel 120 manually, as described in greater detail herein.

In this embodiment, the vacuum port 130 can be used in cooperation with the vein capture channel 120 to capture and substantially immobilize a patient's vein for venipuncture. In one non-limiting example, a practitioner, such as a phlebotomist, can depress the device 100 onto a patient's skin such that the bottom face 110 confronts a target skin area for venipuncture. For example, the practitioner can orient the device 100 such that the vein capture channel 120 covers a portion of the patient's basilica vein in a substantially parallel arrangement. Subsequently, application of vacuum to the vacuum port 130 can engender the target skin area (including subcutaneous physiology) to be urged into the vein capture channel 120 through a pressure differential between the channel 120 and the atmosphere surrounding the device 100. In this embodiment, a vacuum relief bore 140 extends from the top face 112 into the vein capture channel 120 and is configured to allow a practitioner to substantially control the amount of vacuum applied to the channel 120. For example, during a venipuncture procedure, a practitioner can place a finger over the relief bore 140 and adjust the vacuum by variably sealing the opening to the bore 140 on the top face 112. Once the patient's vein is suitably urged into the vein capture channel 120 the vein can remain substantially immobilized by vacuum for venipuncture as described next.

In this embodiment, the device 100 includes a plurality of needle channels 150, 151, 152, 153, respectively that extend from the front face 105 into the vein capture channel 120. In an alternative embodiment, the device 100 can have a single vein capture channel optimally configured for venipuncture as described herein. In this and other embodiments, each needle channel can be configured to receive a particular size, type, shape, length, or other characteristic of a needle or combination needle/catheter system used for venipuncture. In one non-limiting example, needle channel 150 can be configured to receive an 8-gauge hypodermic needle; needle channel 151 can be configured to receive a 10-gauge hypodermic needle; needle channel 152 can be configured to receive a 22-gauge needle; and so on. In this and other embodiments, it can be advantageous to configure the bore size of each needle channel to closely match a particular needle size, so that the needle channel defines a substantially straight pathway to the vein capture channel with a minimum of positional deviation.

In one embodiment, each needle channel can be configured to be substantially equivalent in diameter, providing the capability to receive the same type or size of needle in each channel. In such a configuration, each needle channel can be configured such that the pathway into the vein capture channel 120 follows a different angle of incidence into the captured vein. Such a configuration provides a plurality of guides at different angles that a practitioner can utilize for performing venipuncture.

FIG. 1A illustrates a side view of a venipuncture assist device 200 according to one alternative embodiment. The embodiment of FIG. 1A is similar to the device 100 described herein, wherein like reference numbers indicate similar elements previously described. In this embodiment, the device 200 includes a vacuum manifold 131 in atmospheric communication with a plurality of vacuum relief ports 130a, 130b, 130c. In one embodiment, each vacuum relief port 130a, 130b, 130c, etc. can be configured having a different bore size to provide variability in atmospheric intake through the ports. In this embodiment, the manifold 131 is in atmospheric communication with vacuum port 130, and a second vacuum port 132, each of which extend to, and are in atmospheric communication with the vein capture channel 120.

In this embodiment, the plurality of vacuum ports of the device 200 can be used to fine-tune the amount of vacuum applied to the vein capture channel 120 by a practitioner. For example, vacuum port 130 can be connected to a vacuum source; vacuum will thereby extend to the vacuum manifold 131, the vacuum port 130, the second vacuum port 132, and each of the relief ports 130a-130c. In one practice example, a practitioner can place first, second, and third fingers over the relief ports 130a-130c respectively, thereby providing the greatest vacuum to the vein capture channel 120. The amount of vacuum can be reduced by, for example, lifting the third finger to expose relief port 130c to atmosphere; if further reduction in vacuum is desired, the practitioner can lift first and second fingers to similarly expose relief ports 130a, 130b to atmosphere. Thus, in this and other embodiments, a practitioner can utilize variably-applied vacuum to urge a patient's skin into the vein capture channel 120 for optimal positioning of a vein prior to, and during insertion of a needle through one of the needle ports, e.g., a selected one of needle ports 150-153. This approach can also be useful to prevent collapse of the vein in the event that the amount of applied vacuum is too great.

Referring now to FIGS. 1, 2, and 3 in particular, in this and other embodiments, the device 100 can be formed from two half-portions 101, 102, respectively that are capable of being reversibly mated into an operative configuration as illustrated, e.g., in FIGS. 1, 2, and 3. In such an embodiment, the device 100 can be used first to insert a venipuncture needle or combination needle/catheter system into a patient's vein, e.g., by advancing the needle through one of the needle channels as described herein. Next, after the needle has been suitably advanced into the vein, the two halves 101, 102 of the device 100 can be cleaved so that the device 100 can be removed from around the needle, leaving the venipuncture area open for further treatment, e.g., advancing a catheter into the vein along a path generally defined by the needle itself.

In such an embodiment, each half-portion 101, 102 can be formed, e.g., from molds that incorporate reversible mating functionality. For example, half-portion 101 can include a male member of a latching mechanism, and half-portion 102 can include a corresponding female portion configured to latchingly receive the male member of the latching mechanism (neither male nor female latching members are illustrated in the figures for clarity of the drawings).

In another embodiment, half-portion 101 can include one or more male post members, and half-member 102 can include a corresponding number of female recesses configured and arranged to receive the male post members. Each of the male post members and female recesses can be disposed on mating sides of the half-members 101, 102, respectively, so that a functioning device is formed, e.g., as illustrated in FIG. 1, when the two mating sides are brought into a substantially confronting relationship.

In this and other embodiments, an adhesive of any preferred type can be used to join half-portions in an operative configuration (e.g., as illustrated in FIG. 1) and also provide for their separation when desired. In one approach, the adhesive can be directly applied to either or both surfaces or onto an intermediate member such as an adhesive film that joins mating sections. Certain low tensile strength adhesives or tapes can provide "break-away" functionality so that a practitioner can cleave or separate the half-members 101, 102 easily, as desired. Separating the needle from the device can also be accomplished by providing a membrane between the needle channel opening and surface 110 that can be severed by a tearing action, which can be performed by the practitioner.

In one alternative embodiment, the device 100 can be configured with one or more substantially wedge-shaped "breakaway" portions for separating the device 100 from a needle inserted therein. In one non-limiting example, a breakaway portion can be a wedge-shaped portion having a base that includes a portion of bottom face 110, a height including a portion of front face 105 extending generally from the intersection of the bottom face 110 to a height corresponding to the position of one or more needle channels, e.g., needle channels 150-153, and a planar hypotenuse surface generally corresponding to the path of one or more needle channels, e.g., one of needle channels 150-153.

Referring now to FIGS. 3 and 4, the use of a venipuncture assist device 100 or 200 to perform a venipuncture procedure is illustrated according to one embodiment. FIG. 3 illustrates the procedure in a perspective view while FIG. 4 shows the same procedure in a side-view. In this example, the device 100 can be placed on a patient's skin surface 170 such that the vein capture channel 120 is positioned near, preferably directly over, a target venipuncture site which, in this example, is over a target subcutaneous vein 175. Next, vacuum can be applied to the vacuum port 130. One non-limiting example of a vacuum source that can be used in such a procedure is a vacuum port commonly available in hospitals, ambulances, etc.

Referring to FIGS. 4 and 5 in particular, application of the vacuum to the vacuum port 130 can engender urging of the target area of the patient's skin 170, including the vein 175, into the vein capture channel 120. Urging the skin into the vein capture channel 120 can induce a substantially S-shaped bend 177 in the vein 175 at or near the front face 105 of the device 100 as illustrated. Formation of the S-shaped bend 177 can, in this example, orient the vein in an optimized conformation for receiving a needle 185. In this and other embodiments, an "optimized confirmation" can be one in which a forward bend 179 in the vein is induced such that a forward surface of the vein is oriented preferably at a substantially perpendicular angle with respect to the path of the needle 185 when it is inserted, and where a substantially straightened and stabilized vein portion 181 is created into which the needle can be advanced while minimizing the likelihood of the needle tip puncturing the wall of the vein, e.g., as illustrated in the magnified view portion of FIG. 4.

Still referring to FIG. 4 in particular, in this embodiment, the shape of the induced S-shaped bend 177 can be controlled by variable application of vacuum to the vacuum port 130. Alternatively, or in combination, the amount of applied vacuum can be controlled by the practitioner, e.g., by adjusting the amount of atmospheric air allowed to enter the relief bore 140, e.g., by adjusting a finger position over the bore as previously discussed.

In one approach, a practitioner performing venipuncture with a device 100 or 200 as described herein can adjust the position and orientation of the induced S-shaped bend 177 relative to one or more of the needle channels, e.g., needle channel 150 in FIG. 4, by adjusting the amount of vacuum applied to the vein capture channel as previously described. Thus, the practitioner can "fine-tune" the position and orientation of the vein 175, in particular, the induced S-shaped portion 177 of the vein, prior to inserting the needle 185.

In this embodiment, the target portion of the patient's skin 170 that is urged into the vein capture channel 120 by vacuum can create a substantially straight and stable vein portion 181 into which the needle 185 can be advanced after piercing the vein, e.g., at the forward bend portion 179. Such a configuration can, in this and other embodiments reduce the likelihood of inadvertently advancing the needle through the vein, commonly referred to as "blowing" the vein (extravasation).

Referring again to the magnified view portion of FIG. 4, in this and other embodiments, the incidence angle θ of the needle channel, or channels, if there is a plurality of such can be generally defined by the angle between the needle channel relative to the inner wall of the front face 105, and can be selected such that: 1) a needle, as it is advanced through the channel, will pierce the forward bend portion 179 at an intersection 199 that is generally substantially coaxial with the center axis (dashed line in FIG. 4) of the straightened and stabilized vein portion 181; and 2) the needle will generally advance along the same center axis within the straightened and stabilized vein portion 181 as it is inserted. In one non-limiting example, the angle θ is between about 70 and 85 degrees. In one embodiment, a first needle channel is configured at an angle of about 85 degrees, and a second needle channel is configured at an angle of about 75 degrees. In this and other embodiments, each needle channel can be slightly larger in cross-section than the cross-section of the needle to allow a practitioner a degree of maneuverability when inserting a needle into a vein, if desired. It should be understood throughout this disclosure that the description of advancement of a needle can apply equally to a catheter when a combination needle/catheter system is used by the practitioner.

Referring back to FIG. 1 in particular, in this and other embodiments, the vein capture channel 120 of the device 100 can be configured in any way to facilitate capture and immobilization of various types of veins for performing venipuncture. For example, the width w, the length l, and the height h of the vein capture channel 120 can be configured to accommodate particular vein shapes and sizes; similarly, these variables can be chosen while also taking patient tissue physiology into account. In one example, the vein capture channel 120 can be configured to perform venipuncture as described herein on an "average" patient, wherein the dimensions of the vein capture channel are about 0.200 inches (width, w), about 0.750 inches (length, l), and about 0.200 inches (height, h). In an alternative embodiment, different devices 100 having vein capture channels 120 of a particular size and shape can be used to accommodate various classifications of patients, e.g., pediatric, geriatric, or bariatric patients.

In general, a venipuncture assist device, e.g., device 100, 200 or 300 described herein, can include accessory elements, assemblies or mechanisms configured to assist a practitioner in performing venipuncture procedures. For example, the device 100 can include a light source or assembly such as an LED that can illuminate a target venipuncture area. In such an embodiment, an assembly including a light source providing a desired output spectrum capable of differentiating a vein from surrounding tissue can be advantageous. For example, such an assembly can include an infrared light source. In one embodiment, the device 100 can be constructed from a substantially transparent material, e.g., a transparent plastic, and a controllable LED can be embedded therein. In this and other embodiments, the light source may be remotely located, e.g., not directly attached to, or embedded in the device, and light from the light source can be delivered via one or more transmissive optical elements to the device. One non-limiting example of such a transmissive optical element is an optical fiber.

In one embodiment, a venipuncture assist device of the type described herein can be configured in such a way as to magnify the target venipuncture area. In one non-limiting example, the top face 112 can include, or be configured as a Fresnel- or other type of lens so as to magnify the target venipuncture area. In one embodiment, a Fresnel lens can be etched directly into the top face 112 of the device, particularly if the device is formed of a clear, solid material. In another embodiment, a traditional convex lens can be adhered to, or integrated into the top face 112.

Figure 8:
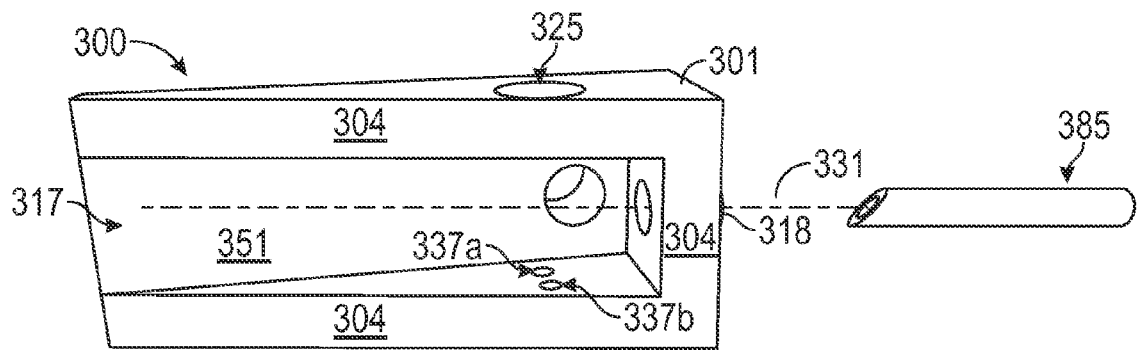
Figure 9:
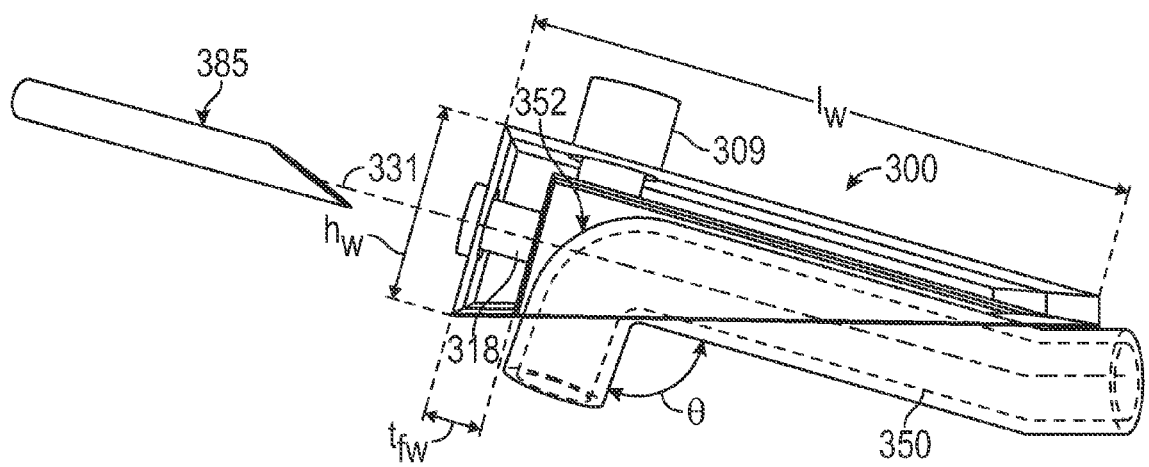

Referring now to FIGS. 5-9, a venipuncture assist device 300 (hereinafter "device") is shown according to one embodiment, wherein: FIG. 5 is an isometric view of the device 300; FIG. 6 is a right-side elevation view of the device 300; FIG. 7 is a left-side elevation view of the device 300; FIG. 8 is an isometric bottom-view of the device 300; and FIG. 9 shows the device 300 in a left-side elevation view with the left side 305 removed to illustrate internal components.

In this embodiment, the device 300 is substantially wedge-shaped, having a right side 301, a front side 302, a top side 303, a bottom side 304, and a left side 305 as illustrated. The device 300 further includes an inner cavity 317 for receiving a portion of a patient's vein 350 that is defined by the interior walls of the right side 301 and the left side 305, an inner top wall 351, and an inner front wall 353 as illustrated, e.g., in FIGS. 8 and 9. The inner cavity 317 can provide the same or similar functionality as that of the vein capture channel 120 described herein with respect to capturing and immobilizing a target vein portion for venipuncture.

In this embodiment, the device 300 includes a vacuum port 310 defined by the inner wall of cylinder 309 which extends through the top side 303 and is in atmospheric communication with the inner cavity. Although not illustrated in FIGS. 5-9, cylinder 309 can be configured to reversibly couple to a tube or other lumen extending from a vacuum source so that a vacuum can be applied to the inner cavity. For example, a portion of the cylinder 309 extending from the top side 303 can include an internally- or externally-threaded portion configured as a male or female portion of a Leur-lock system.

In this embodiment, the device 300 includes a needle port 320 disposed on the front side 302 that is defined by an interior wall of cylinder 318 and extends into the inner cavity. In this embodiment, the cylinder 318 can have a length dimension and be oriented such that it is capable of guiding a needle 385 along an axis into the inner cavity at an optimized angle and location for piercing a vein. In FIGS. 5-9, the cylinder axis is illustrated by dashed line 331 and is generally a line joining the center of each end opening of the cylinder 318.

In this and other embodiments, the central axis of the cylinder can be configured at an angle relative to the front side 302 plane that optimizes the approach path of the needle 385 as it enters the inner cavity. For example, the central axis of the cylinder 318 can be configured such that when a vein is captured within the inner cavity (as described more completely herein), an elongate portion of the vein, e.g., the portion 1 in FIG. 6, has a substantially coaxially-aligned relationship with the cylinder 318 axis as illustrated, e.g., in FIG. 6.

In one embodiment, the device 300 can include indicia to convey an optimal needle orientation to the practitioner, specifically an orientation about the long axis of the needle, such that when the needle is inserted into the system, the likelihood of piercing an unintended portion of the vein is minimized. In one example, the front side 302 can include a tick mark (not illustrated in FIGS. 5-9) for aligning the tip and the heel of the needle in a particular orientation that minimizes the likelihood of the tip contacting the inner wall of the vein during venipuncture. In this and other embodiments, the cylinder 318 can be configured with spatial tolerances such that the needle can be rotated upon insertion.

Referring to FIG. 9 in particular, in this embodiment, the device 300 is configured to engender a bend in a target portion of a patient's vein when urged into the inner cavity 317 by way of applied vacuum as previously described. In this embodiment, the bend angle θ of the vein 350, e.g., in FIGS. 6 and 9 can be controlled by one or more variables. For example, the bend angle can be controlled by the amount of vacuum applied to the inner chamber, which can control the extent to which a forward portion 352 of the vein 350 is urged toward the inner top wall 351. In another example, the wedge-like dimensions of the device 300 can be configured to optimize the bend angle. For example, the wedge height $h_w$, wedge length $l_w$, or any other dimension can be configured to optimize the bend angle θ.

Similarly, in this and other embodiments, the dimensions of the wedge-like device 300 can be configured for optimized use with certain patient populations, e.g., pediatric, geriatric or bariatric populations, or for use with patients having thin or fragile vasculature, or for other reasons. For example, a device 300 can be configured for use primarily on pediatric patients, where the dimensions of the wedge-like device 300 are correspondingly smaller than that of a system configured for adult use.

Still referring to FIG. 9, in this and other embodiments, the device 300 can be configured to provide a safety aspect that limits the distance a needle 385 can be inserted into a vein 350 captured within the inner channel, to minimize the likelihood of extravasation. In this embodiment, such a safety aspect can be realized by providing a front wall thickness, denoted $t_{fw}$ in FIG. 9 that limits the insertion length of the needle 385 into the inner cavity. In such embodiments, cylinder 318 can have length along the cylinder axis that substantially corresponds with the front wall thickness.

In one example, the device 300 can have a front wall thickness of about one-half to one-third the length of a hypodermic needle of a particular length, such that the needle can only be inserted about half-way or two-thirds of the way into the inner cavity, respectively. It will be understood that a wide range of needle sizes and lengths are available in medical markets and that the front wall thickness can be chosen to accommodate such variability while providing the advantageous safety aspect provided herein.

Referring now to FIGS. 6 and 7 in particular, in this and other embodiments, the device 300 (or device 100, 200 or 500 described herein) can be configured to provide verification of vein capture during use. In general, a feature, system, or other configuration can be integrated that provides a practitioner the ability to verify that a targeted portion of a vein 350 (e.g., a portion of skin on a subject's forearm) has been urged into the inner cavity and is in a ready configuration for venipuncture. In general, such a "ready position" can be a vein configuration in which the vein, as urged into the inner cavity under vacuum, is bent at an angle θ at or near the front side 302 substantially similar to the exemplary vein configurations illustrated in FIGS. 4, 5-7 and 9.

In this embodiment, the device 300 is configured to include an optical vein capture verification system. Referring to FIG. 6, in this embodiment, the left side 301 includes a first aperture 325 configured to securely receive a light source (not shown in FIGS. 5-9) such that light from the light source can be directed into the inner cavity. One exemplary light source is a terminal end portion of a fiber optic coupled to a light source providing a selected light spectrum. Referring to FIG. 7, in this embodiment, the right side 305 includes second and third apertures, 337a, 337b, respectively, disposed substantially opposite to the first aperture 325. In this embodiment, the second and third apertures can be configured to securely receive first and second light detectors (not shown in FIGS. 5-9) capable of detecting light from the light source; or, in an alternative embodiment, first and second light output channels such as fiber optic cables.

In this embodiment, vein capture verification can be realized by optically detecting the presence or absence of a vein 350 between the first aperture 325 and the second aperture 337a, or between the first aperture 325 and the third aperture 337b, or both. Optical detection of the vein can be realized by a variety of optical detection or spectroscopic methods. In some embodiments, electronic circuitry in signal communication with light detectors disposed within first (337a) or second (337b) light detectors, or light detectors coupled to the light output channels can be configured and utilized to measure or detect the amount of light absorbed by the patients tissue, vasculature, or both within the inner cavity 317.

For example, first and second photodetectors (not shown in FIGS. 5-9) can be housed within the second (337a) and third (337b) apertures and configured to detect light from an oppositely-disposed light source housed in the first aperture 325. Before the target venipuncture area is urged into the inner chamber 317 under vacuum, e.g., as previously described, the first and second photodiodes can receive a baseline flux or intensity reading. In one approach, an additional baseline reading of flux or intensity can be established by the practitioner that is representative of conditions that will not enable a successful venipuncture, e.g., an intensity reading of tissue devoid of a vein. As the target venipuncture area is urged into the inner chamber 317 under vacuum, the amount of light reaching the second photodetector (within the third aperture 337b) will begin to be attenuated due to absorption and scattering within the tissue. At this point, an electronic detection circuit in signal communication with the photodiodes can detect that the intensity of the second photodiode is less than that of the first; the circuit can cause an indicator light to illuminate, e.g., a yellow light on the top side 303 (not shown in FIGS. 5-9) to indicate that the vein is not fully seated within the inner cavity. As the vein is urged further into the inner cavity, light received at the second photodiode can become further attenuated due to the greater light absorbing aspect of a vein relative to surrounding tissue. In a similar fashion, the electronic detection circuit can detect this attenuation and cause a second light, e.g., a green light on the top side 303 to illuminate, indicating to the practitioner that the vein is in an optimized configuration for venipuncture.

In some embodiments, the device 300 can include one or more electronic circuits (not illustrated) configured to perform diagnostic functions as a function of light received at one or more photodetectors. For example, an electronic circuit can include a storage module configured to store software logic instructions for carrying out analysis of photodetector signals. In such an embodiment, the circuit can include a processor, memory, signal input and output ports, stored logic functions, and a logic repository, all of which can be in electronic signal communication with each other and configured to carry out diagnostic, vein location verification functions, or other functions. In one example, the circuit, light source, and photoreceptors can be configured to optically detect fluid flow within the vein so as to distinguish light attenuation occurring from tissue absorption versus light attenuation occurring from the light source passing through the vein. In one embodiment, the light source can be configured to producing light in the infra-red or near infra-red portion of the electromagnetic spectrum, and the light detector can be an infra-red or near infra-red photodetector.

Referring back to FIG. 5, in this embodiment, the device 300 can be formed from a first body half 302a and a second body half 302b, although the device 300 can alternatively be formed as a unitary body. Each body half can be reversibly mated together to form the device 300, e.g., as illustrated in FIG. 5. In this embodiment, the separable body halves 302a, 302b provide the capability to remove the system from the target venipuncture area once a needle has been introduced into the vein.

For example, a practitioner can apply the device 300 to the target venipuncture area and apply vacuum through the vacuum port 310 to cause the target venipuncture area to be urged into the inner chamber. Once the vein is in the proper orientation, e.g., as verified by optical methods described herein, or by visual confirmation, the practitioner can insert a needle 385 through the needle port 320, into the inner cavity, thereby piercing the vein at or near the forward portion of the vein 352. Optimally, the forward portion of the vein 352 can be oriented substantially normal to the incidence angle of the needle 385. The practitioner can then advance the needle as far as necessary to achieve proper venipuncture. At this point, the two body halves 302a, 302b can be separated, leaving the needle 385 inserted and undisturbed within the patient's tissue. Alternatively, the practitioner can advance a catheter or other lumen along the needle, into the vein, as is common practice when starting intravenous therapy, for example, prior to separating and removing the two body halves 302a, 302b. In an alternative practice, the device 300 can be left intact and secured to the patient using, e.g., tape, bandages, or other methods.

Referring now to FIGS. 10 and 11, a venipuncture assist system (hereinafter VAS) is illustrated according to one embodiment. In this embodiment, the VAS includes a vein finder assembly 400 and a venipuncture assist assembly 500.

In this embodiment, the vein finder assembly 400 includes a locator ring 401. The locator ring 401 is configured for cooperative use with an optical vein finder assembly (hereinafter OVFA) 450 which is configured to assist in locating a subcutaneous vein for venipuncture. In this embodiment, the locator ring 401 has a center aperture as illustrated which is intended to be placed over a target venipuncture area. In FIG. 10, the target venipuncture area includes a subcutaneous vein illustrated in dashed lines. The locator ring 401 further includes first (402) and second (403) recesses that are configured to receive tab members 452, 453 respectively of OVFA 450 as described in greater detail below.

In this embodiment, the OVFA 450 includes the aforementioned tab members 452, 453 which are configured to be inserted into the first (402) and second (403) recesses of the locator ring 401 when first attempting to find a vein for venipuncture. The top portion of FIG. 10 illustrates a bottom-view of the OVFA 450 showing an input light (hv) source 455 and two axially-aligned light receivers 457, 459. Referring to the perspective view in the bottom of FIG. 10, in this embodiment, fiber optic cables are used to deliver light to the target venipuncture area (input light source 455) and receive reflected light therefrom via light receivers 457, 459. In this embodiment, each of the light receivers 457, 459 are coupled to an electronic optical detection circuit such as a photodiode. It should be understood that a greater or fewer number of input light sources and/or receivers can be used in alternative embodiments.

In this embodiment, the OVFA 450 provides assistance in locating a vein for venipuncture by taking advantage of the light absorptive properties of a blood vein relative to surrounding tissue. In this and other embodiments, the OVFA 450 can include one or more light output channels, e.g., fiber optics, that extend from a bottom surface 451 of the OVFA that is configured to confront the skin of a patient and lead to a light detection device such as a photodiode. The signal of the light detection device can be coupled with an electronic circuit configured to measure the signal, such that a user of the OVFA can, through audio or visual cues, detect local areas on a patent's skin where light is maximally absorbed by a vein. For example, a photodiode can be in signal communication with an electronic circuit capable of displaying a measure of measured light absorption, e.g., a minimum photodiode signal strength, using a lighted scale, a series of LED lights that indicate a measure of signal strength, an auditory signal, or other approaches.

To locate a vein, the OFVA 450 is first coupled with the locator ring 401 by inserting tab 452 (453) into recess 402 (403). Next, the target venipuncture area is illuminated by, e.g., input light source 455. The VAS can then be rotated or shifted on the skin until the scattered light, detected by each of the light receivers 457, 459 is minimized. In such a circumstance, it can be likely that a subcutaneous vein is axially aligned with the light receivers 457, 459, thereby defining an insertion axis for advancing a venipuncture needle into the located vein. At this point, the OFVA 450 can be decoupled from the locator ring while maintaining the orientation and position of the locator ring 401 on the patient's skin. Maintaining the orientation of the locator ring provides the ability to couple a venipuncture assist assembly 500 (described below) thereto in such a way that the vein capture channel of the venipuncture assist assembly is already substantially aligned with the vein as described in greater detail below.

In this and other embodiments, a variety of combinations of light input and output channels can be used in an OFVA. For example, in one embodiment, the OFVA can be formed of a substantially clear material such as a glass or silicone material to allow ambient light to propagate therethrough and onto a target venipuncture area, e.g., a portion of a patient's skin. In this example, a light input channel may not be necessary if there is sufficient ambient light to be able to detect changes in light absorption through the light output channels as the OFVA is moved about on the target venipuncture area. Continuing this example, the OFVA can include two light output channels spaced apart so as to define an insertion axis. Without wishing to be bound by theory, the measured light output signal from each light output channel should be minimized when each are positioned over a portion of a subcutaneous vein. Such a configuration can thereby define an insertion axis that is substantially parallel with a subcutaneous vein.

In another example, a single light input channel can provide a source of light illumination on the target venipuncture area, and a single light output channel can provide the capability of measuring absorbed light within the area. In this example, an insertion axis can be similarly defined by moving the OFVA about the target venipuncture area until a measured light intensity signal is minimized. In this example, without wishing to be bound by theory, the minimization of measured light intensity can be caused by two factors: first, the total amount of input light will be minimized when the light input is positioned directly over a vein; the second contributor to minimization of light intensity signal can be caused when the light output channel is similarly positioned over a vein.

It should be understood that other combinations, configurations and arrangements of light input and output channels can be chosen to optimize vein finding functionality of the OFVA and for other considerations, without limitation.

Referring to FIG. 11, in this embodiment, the venipuncture assist assembly 500 is functionally similar to the venipuncture assist devices previously described herein, e.g., devices 100, 200 or 300. In this embodiment, the venipuncture assist assembly 500 includes a flexible disk 501 configured generally similar to a suction cup, having tabs 502, 503 protruding therefrom as illustrated. Tabs 502, 503 are similar to tabs 452, 453, in that they are configured to be inserted into recesses 402 and 403 respectively of the locator ring 401. The venipuncture assist assembly 500 further includes a recessed vein capture channel on a bottom portion of the disk 501 beneath vacuum manifold 527 (not illustrated in FIG. 11 for clarity) that is similar to the vein capture channel 120 described herein. Vacuum line 510 is in atmospheric communication with vacuum manifold 527 and the vein capture channel, and is configured to provide the capability to reduce the atmospheric pressure of the vein capture channel. Similar to the previously-described embodiments, reducing the atmospheric pressure within the vein capture channel can engender urging of tissue and a subcutaneous vein into the vein capture channel in an optimized configuration to be pierced by a venipuncture needle. Venipuncture assist assembly 500 further includes at least one needle channel 515 extending from a front face 509 into the vein capture channel that is configured and oriented to allow a needle to be advanced therethrough, at an optimized incidence angle so that the needle can be advanced into the vein as previously described. In this and other embodiments, the venipuncture assist assembly 500 can include a cleavage extending from the vein capture channel to the front face that is configured to allow the venipuncture needle to pass therethrough so that the venipuncture assist assembly 500 can be removed from the venipuncture site while leaving the venipuncture needle or needle/catheter assembly inserted into the patient's vein.

In this embodiment, venipuncture assist assembly 500 further includes an optical vein capture verification system (OVCVS) 600 similar to that described with respect to FIG. 6. In this embodiment, the OVCVS 600 includes a main housing 601 having a substantially hollow interior and is configured to fit over the venipuncture assist assembly 500. The OVCVS 600 includes a slot 615 into which the vacuum port 510 fits when covering the venipuncture assist assembly 500. The OVCVS 600 further includes a light input 605 and a light output 610, each of which can be, for example, lengths of a fiber optic cable that deliver light into the housing 610 and receive light to be transmitted to, e.g., a photodetector, respectively. The position of the light input 605 and light output 610 on the housing 601 are such that they define a path through the vein capture channel wherein a vein would be positioned in an optimal position for venipuncture, similar to the configuration of the vein 350 illustrated in FIG. 9. The OVCVS 600 can be used to verify vein placement in the channel prior to performing venipuncture by optically detecting the presence of a vein, e.g., by supplying requisite vacuum to the vein capture channel until the input light is maximally attenuated, as detected by an optoelectronic device in optical communication with the light output 610. In general, the VAS 400 and OVCVS 600 can be configured or adapted for use with any of the venipuncture assist devices described herein and used for the same or similar purpose.

In general, a venipuncture assist device of the type described herein can be formed from any desired material that allows its function as described. Exemplary materials include, without limitation, glasses, plastics, especially flexible plastics and silicone. The devices described herein can be formed, for example, using injection molding or other techniques. Devices of the type described herein can be configured to achieve the described functionality while accommodating needles, catheters, combination needle/catheter systems and other medical devices of various shape, size and purpose. In general, vacuum can be applied to the inner chamber using a remote vacuum source, e.g., those found in hospitals, ambulances, etc.; however, other vacuum sources can be used. For example, a venipuncture assist device, e.g., device 100, 200, 300 or 500 can include a manual pump mechanism that allows a practitioner to manually create a vacuum for the purposes of urging tissue into a vein capture channel as described herein. For example, a one-way bulb mechanism providing one-way air flow can be connected at one end to a vacuum port, e.g., vacuum port 310, while another end of the bulb purges air to the atmosphere. Squeezing the bulb can cause air to be evacuated from the inner cavity, thereby causing a vacuum to be created. The void adjacent to area 352 of the vein may be filled by varying the geometry of the interior surfaces of vacuum cavity to influence the positioning of the vein.

In one embodiment, the interior of a venipuncture device can have a curved or contoured surface to maximize vacuum sealing with the patient's skin. For example, referring to FIG. 9, the intersection of the interior walls of the front side 302 and the top side 303, shown at a right angle in FIG. 9, can be made to include a connecting contour that generally matches the forward portion 352 of the vein 300.

In one alternative embodiment, a venipuncture device includes a pierceable membrane on front side 302. In this embodiment, the front side 302 can be devoid of a needle channel as previously described, to allow a practitioner additional freedom in performing a venipuncture procedure. In this embodiment, the pierceable membrane can be translucent, or clear, to allow the practitioner to visualize the anatomy within the device, e.g., within the inner chamber. Such a pierceable membrane can be formed of any suitable material, including plastics, rubbers, or other materials; in general, however, the membrane material should be capable of maintaining a vacuum seal within the inner cavity in preferred embodiments.

A number of illustrative embodiments have been described. Nevertheless, it will be understood that various modifications may be made without departing from the spirit and scope of the various embodiments presented herein. Accordingly, other embodiments are within the scope of the following claims.

What is claimed is:

1. A venipuncture assist device, comprising:
   a main body having a bottom surface portion for confronting a target venipuncture tissue site;
   a vacuum port disposed on said main body in atmospheric communication with a vein capture channel that, when a vacuum source is applied thereto, creates a vacuum urging force within said vein capture channel;
   wherein said vein capture channel is disposed within said bottom surface portion and is configured to receive a vein portion of said target venipuncture tissue site therein when said vacuum urging force is created; and
   a first needle channel that extends from a front face of said main body to said vein capture channel that is configured to receive a venipuncture needle and arranged so that said venipuncture needle can be advanced into said vein portion at a first incidence angle.

2. The venipuncture assist device of claim 1, wherein said first incidence angle is substantially coaxial with a long axis of said vein capture channel.

3. The venipuncture assist device of claim 1, wherein said vein capture channel is configured to engender a bend in said vein portion when urged therein to form an optimized vein-piercing configuration.

4. The venipuncture assist device of claim 1, further comprising a vacuum relief bore in atmospheric communication with said vacuum port that is configured to provide control of a magnitude of said vacuum urging force by a user.

5. The venipuncture assist device of claim 1, further comprising a second needle channel that is different from said first needle channel that extends from said front face of said main body to said vein capture channel for receiving a venipuncture needle, and furthermore arranged so that said venipuncture needle can be advanced into said vein portion at a second incidence angle that is different from said first incidence angle.

6. The venipuncture assist device of claim 5, wherein an inner diameter of said first needle channel is different than an inner diameter of said second needle channel.

7. The venipuncture assist device of claim 1, wherein said first needle channel has an inner diameter slightly greater than a diameter of said venipuncture needle.

8. The venipuncture assist device of claim 1, wherein said first needle channel has an inner diameter slightly greater than a diameter of a venipuncture catheter.

9. The venipuncture assist device of claim 1, wherein said main body is configured to provide a capability of removing said main body from said target venipuncture tissue site while maintaining a position of said venipuncture needle having been advanced into said vein portion via said main body.

10. The venipuncture assist device of claim 9, wherein said main body comprises a cleavage extending from said vein capture channel to said front face that is configured to allow said venipuncture needle to pass therethrough.

11. The venipuncture device of claim 9, wherein said main body comprises first and second reversibly-joinable sections configured to provide a capability of cleaving said main body into at least two parts.

12. The venipuncture device of claim 11, wherein said first and said second sections are reversibly joinable by an adhesive film disposed therebetween.

13. The venipuncture device of claim 1, further comprising an optical detection system configured to distinguish light absorption between skin tissue and the vein portion disposed within a selected area of said vein capture channel.

* * * * *